United States Patent
Beraja et al.

(10) Patent No.: US 8,000,980 B2
(45) Date of Patent: *Aug. 16, 2011

(54) MEDICAL INFORMATION SEARCHING AND INDEXING METHOD AND SYSTEM

(75) Inventors: Roberto Beraja, Coral Gables, FL (US); Victor Beraja, Coral Gables, FL (US); Esther Beraja, Coral Gables, FL (US)

(73) Assignee: IBEZA, LLC, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/928,773

(22) Filed: Oct. 30, 2007

(65) Prior Publication Data

US 2008/0052129 A1    Feb. 28, 2008

Related U.S. Application Data

(62) Division of application No. 11/191,304, filed on Jul. 28, 2005, now Pat. No. 7,464,042.

(51) Int. Cl.
  *G06Q 10/00* (2006.01)
  *G06Q 50/00* (2006.01)
(52) U.S. Cl. .......................................................... 705/2
(58) Field of Classification Search ................. 705/2–3
  See application file for complete search history.

(56) References Cited

U.S. PATENT DOCUMENTS

| | | | | |
|---|---|---|---|---|
| 5,583,758 A * | 12/1996 | McIlroy et al. | ........ | 705/2 |
| 5,924,073 A | 7/1999 | Tyuluman et al. | ........ | 705/2 |
| 5,924,074 A * | 7/1999 | Evans | ........ | 705/3 |
| 5,946,659 A | 8/1999 | Lancelot et al. | ........ | 705/3 |
| 6,188,988 B1 | 2/2001 | Barry et al. | ........ | 705/3 |
| 6,283,761 B1 * | 9/2001 | Joao | ........ | 434/236 |
| 6,684,276 B2 | 1/2004 | Walker et al. | ........ | 710/73 |
| 6,827,670 B1 | 12/2004 | Stark et al. | ........ | 482/9 |
| 6,988,088 B1 | 1/2006 | Miikkulainen et al. | ........ | 706/14 |
| 7,256,708 B2 | 8/2007 | Rosenfeld et al. | ........ | 340/870.01 |
| 2001/0012913 A1 | 8/2001 | Iliff | ........ | 600/300 |
| 2002/0049612 A1 * | 4/2002 | Jaeger et al. | ........ | 705/2 |
| 2002/0116224 A1 | 8/2002 | Hengerer et al. | | |
| 2002/0120471 A1 | 8/2002 | Drazen | ........ | 705/3 |
| 2002/0143579 A1 * | 10/2002 | Docherty et al. | ........ | 705/2 |
| 2003/0055679 A1 | 3/2003 | Soll et al. | ........ | 705/2 |
| 2003/0120512 A1 | 6/2003 | Dengler | ........ | 705/2 |
| 2003/0212576 A1 | 11/2003 | Kim | ........ | 705/2 |
| 2003/0233250 A1 | 12/2003 | Joffe et al. | ........ | 705/2 |
| 2004/0078220 A1 | 4/2004 | Jackson | ........ | 705/2 |
| 2004/0153338 A1 | 8/2004 | Kim et al. | ........ | 705/2 |
| 2004/0260577 A1 | 12/2004 | Dahlin et al. | ........ | 705/2 |
| 2004/0267572 A1 | 12/2004 | Emery et al. | ........ | 705/2 |

OTHER PUBLICATIONS

Medical Expert Systems, May 20, 2005, http://www.computer.privateweb.at/judith/name_3.htm.

* cited by examiner

*Primary Examiner* — Gerald J. O'Connor
*Assistant Examiner* — Sheetal R Rangrej
(74) *Attorney, Agent, or Firm* — Mark R. Malek, Esquire; Zies Widerman & Malek

(57) ABSTRACT

A method for assisting a medical professional with making a medical related decision based on patient information includes providing access to a plurality of databases containing medical related information and at least one rule governing medical care. The method may also include searching for patient information on at least one of the plurality of databases providing search results of the patient information regardless of the location of the patient information.

29 Claims, 9 Drawing Sheets

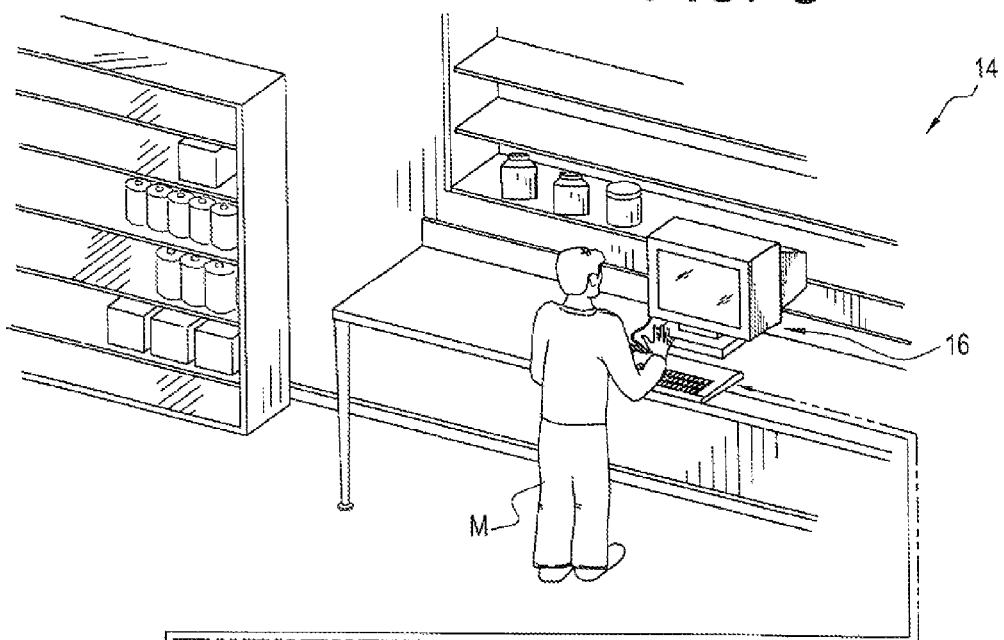
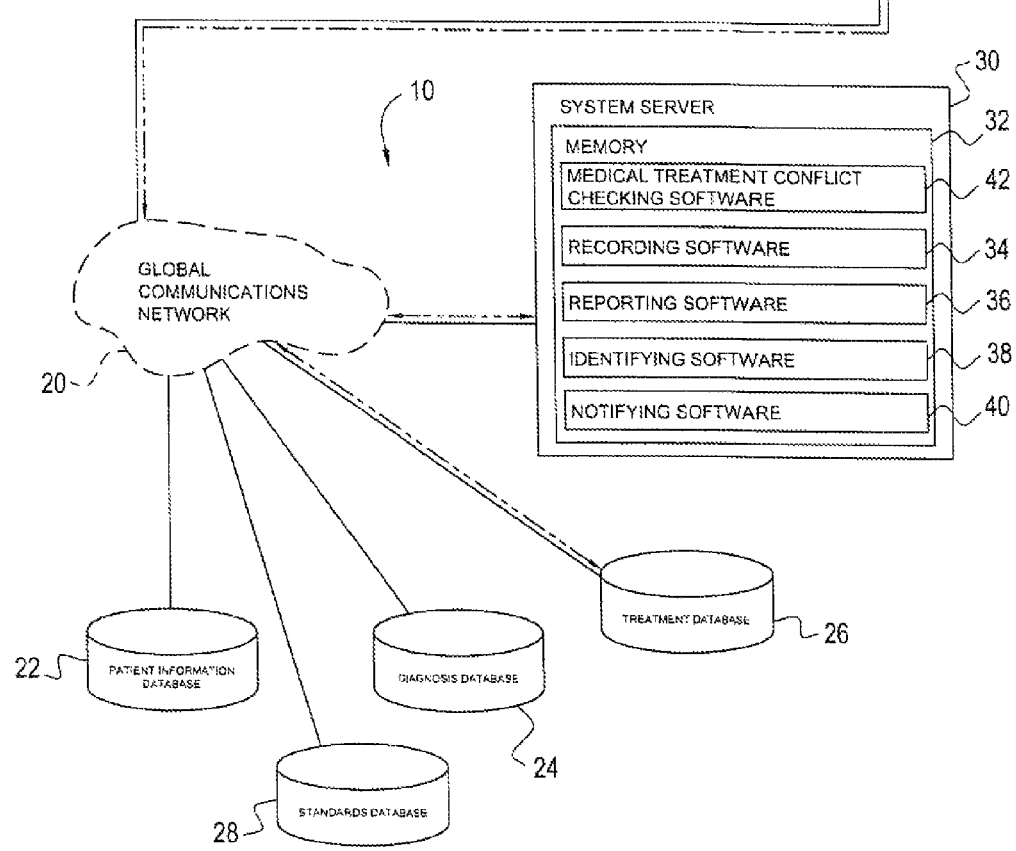
FIG. 6

MEDICAL INFORMATION SEARCHING AND INDEXING METHOD AND SYSTEM

RELATED APPLICATIONS

This application is a divisional of U.S. patent application Ser. No. 11/191,304, filed on Jul. 28, 2005, now U.S. Pat. No. 7,464,042, which issued on Dec. 9, 2008, by the inventors of the present application, the entire contents of which are incorporated herein by reference.

FIELD OF THE INVENTION

The present invention relates to the field of medical diagnosis, medical treatment and medical tracking and, more particularly, to the field of monitoring medical professionals that make medical diagnoses and prescribe medical treatments, and related methods.

BACKGROUND OF THE INVENTION

Systems and various types of software have been extensively used to assist medical professionals in making diagnoses of patient conditions, and to assist medical professionals in prescribing particular courses of medical treatments for those diagnoses.

For example, a medical software system provided under the trade name "ACORN" is a system that was developed by the Accident & Emergency Department of Westminster Hospital in London that advises on management of chest pain patients in the emergency room. Another medical software system is provided under the trade name "ADE Monitor" and is being developed by the Washington University School of Medicine Department of Internal Medicine division of Medical Informatics. This system was developed to monitor patient clinical data for potential adverse drug events. Yet another similar medical software system is offered under the trade name "CADIAG-II" and has been developed by the Department of Medical Computer Sciences. University of Vienna, the Department of Internal Medicine III, section of Rheumatology and the Department of Internal Medicine I, Divisions of Oncology. University of Vienna Medical School. This system is directed to colon diseases, and is a computer-assisted consultation system to support the differential diagnostic process in internal medicine.

U.S. Published Patent Application No. 2002/0120471 by Drazen discloses a system that includes a database for storing a plurality of different medical guidelines for different health conditions, and for storing historical patient information data for a plurality of patients. The patient information is gathered over a global communications network, i.e., the Internet, and evaluated to provide a patient specific risk report based upon the medical guidelines stored in the database. A physician's treatment plan may be generated to reduce patient risk based on the medical guidelines.

This system, however, may be disadvantageous as it allows a physician to become reliant upon a system, instead of the physician's own medical knowledge. Further, this system fails to monitor performance of the physician with respect to whether the medical treatment prescribed by the physician is proper. Accordingly, such a system may cause a waste in resources.

U.S. Published Patent Application No. 2002/0143579 by Docherty et al. discloses a system that identifies opportunities for direct physician intervention to improve prescribing practices and patient compliance. More specifically, the system collects information relating to a physician's prescription practice, and analyzes that information with respect to expert guidelines. The system identifies deviations from expert guidelines and provides the physician with intervention information.

A system for assessing physician performance that includes a database to store patient/physician contact is disclosed in U.S. Pat. No. 5,924,073 to Tyuluman et al. An evaluator is coupled to the database to evaluate the data using statistical analysis. This system may be used to define a standard of care for a core element of patient population. The standard of care may be updated based upon more efficient and more effective treatments, and the system may identify doctors who perform outside the defined standard of care. These systems, however, do not take into account the several standards that a physician must analyze when prescribing medical treatments, i.e., hospital standards, medical standards, insurance standards, etc.

U.S. Published Patent Application No. 2003/0055679 by Soll et al. discloses a computerized patient management system that includes a patient module, a physician module, and a database. The system allows patients to input their patient information into the patient module. The database includes medical assessment and treatment information used to analyze the patient information and generate a report. The physician may edit the report and add assessment and management plans. The physician may also select patient educational materials to be provided to the patient, along with a health summary, at a patient interview. This system, however, relies heavily on the patients' ability to properly enter their patient information. Further, this system provides access to persons that do not have as much medical knowledge as a trained medical professional.

SUMMARY OF THE INVENTION

In view of the foregoing background, it is therefore an object of the present invention to provide a system that enhances patient healthcare by reducing possible medical errors. It is also an object of the present invention to provide a system that monitors medical care that patients receive and the performance of medical professionals to provide enhanced healthcare services by reducing possible medical errors. It is further an object of the present invention to monitor and report the outcomes of medical treatments. It is still further an object of the present invention to provide a system for enhancing the efficiency of medical chart review and the time for receiving payment for medical services and treatments. It is yet another object of the present invention to provide secured indexing and searching capabilities so that information regarding a patient may be readily located.

It is further an object of the present invention to provide a system that greatly decreases the time for an insurance company to submit payment to a medical professional. It is still further an object of the present invention to provide updated medical treatment information, such as new medical standards and procedures, to medical professionals. It is yet another object of the present invention to reduce any waste of medical resources.

These and other objects, features, and advantages in accordance with the present invention are provided by a medical professional monitoring system that includes a user interface in communication with a global communications network for use by a medical professional. The system may also include a patient information database, a diagnosis database, and a medical treatment database, each of which may be in communication with a global communications network.

The patient information database may include patient information for a plurality of registered patients accessible by the medical professional. The diagnosis database may include diagnosis information accessible by the medical professional, and the medical treatment database may include medical treatment information accessible by the medical professional.

The system may also include a server in communication with the global communications network. The server may include a recording system to record the medical treatments selected by the medical professional. The recording system may also track the medical treatments selected by the medical professional for compliance with a predetermined standard selected from a plurality of predetermined standards. The recording system advantageously enhances training of medical professionals, which, in turn, enhances the quality of medical care provided to patients by reducing possible medical errors.

The system may further include a standards database in communication with the global communications network. The standards database may include the plurality of predetermined standards, and may be updateabie. The plurality of predetermined standards may, for example, be hospital standards, insurance standards, medical treatment standards, pharmaceutical standards, medical office standards, or emergency response standards. Accordingly, the system may advantageously coordinate practice guidelines from several sources, such as insurance and federal programs, hospitals and other medical facilities, medical practices and medical professionals.

Similarly, the patient information, diagnosis, and medical treatment databases may also be updateable. Updating these databases advantageously provides medical professionals with up to date medical information, thereby enhancing the quality of medical care.

The system may also include a reporting system for reporting a medical professional that selects a medical treatment that is not in compliance with at least one of the plurality of predetermined standards in the standards database. The medical professional may, for example, be reported to a reporting agency. The reporting system may advantageously enhance the ability of the system to monitor medical professionals that repeatedly select medical treatments that are not in compliance with predetermined standards. The monitoring system may also recommend training for those medical professionals.

The system may further include a medical professional identification device for identifying the medical professionals that access the databases. The system may also include a notification system in communication with the global communications network for notifying an insurance company of patient treatment. The notification system may advantageously decrease the time in which medical professionals receive payment from insurance companies for medical treatment that they prescribe to patients.

The medical professional may, for example, be a physician, a physician assistant, a nurse, a pharmacist, a dietician, a laboratory technician, or an emergency responder. The system is advantageously adapted to be used by any medical professional that has interaction with patients.

A method aspect of the present invention is for monitoring a medical professional. The method may comprise providing the medical professional access to the patient information database, the diagnosis database, and the medical treatment database. The method may also include monitoring the medical treatment selected by the medical professional for compliance with at least one predetermined standard selected from a plurality of predetermined standards on the predetermined standards database.

Another method aspect of the present invention is for selecting a medical treatment. The method may comprise accessing and updating patient information of a registered patient in a patient information database, accessing diagnosis information in a diagnosis database, and selecting a medical treatment for the patient based upon the diagnosis information in the diagnosis database. The method may further include evaluating the selected medical treatment for conflict with an existing medical treatment.

BRIEF DESCRIPTION OF THE DRAWINGS

FIGS. 4-6 illustrate the various medical professional user sites illustrated in FIG. 1 using the medical professional monitoring system according to the present invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
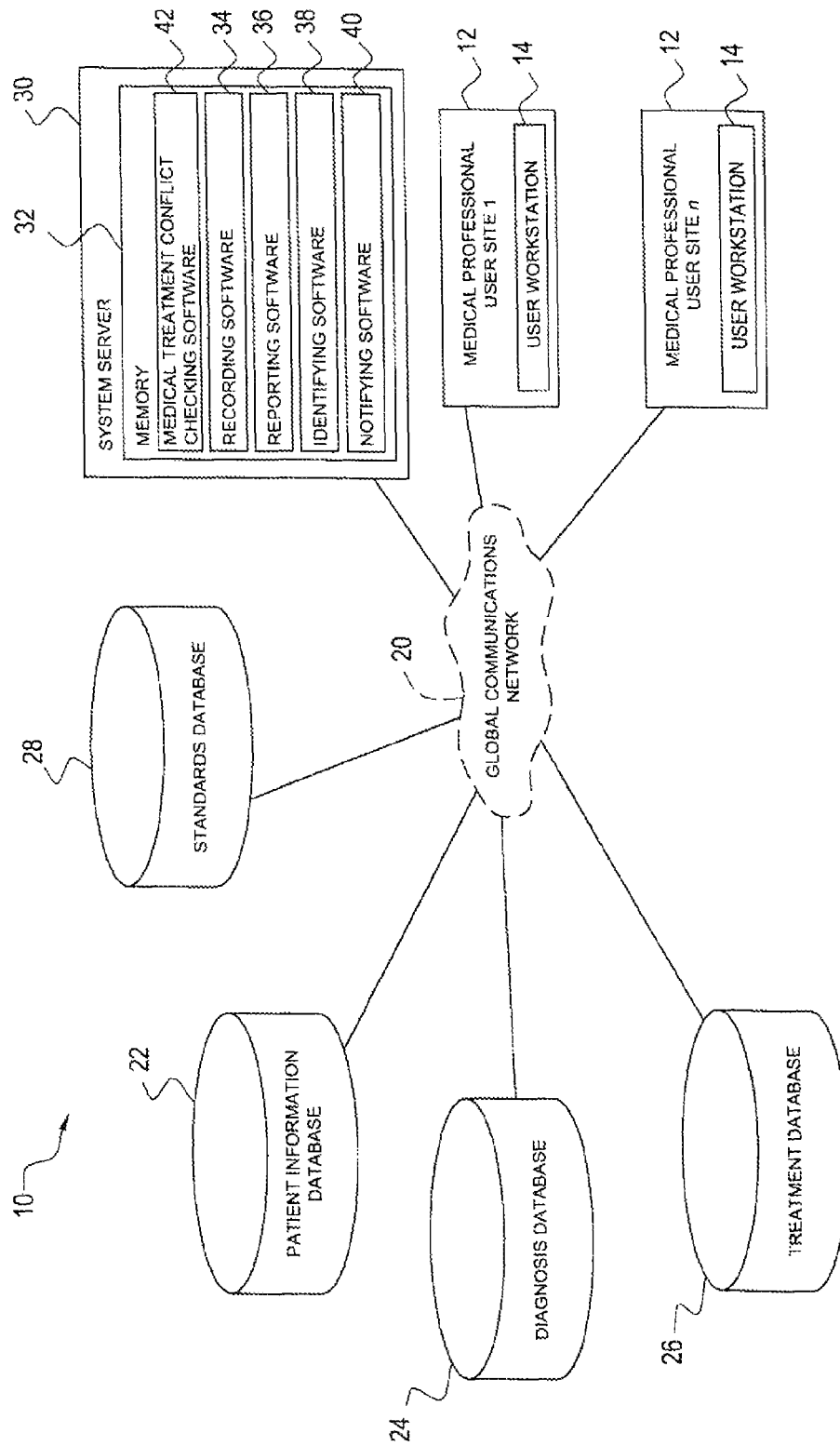
FIG. 1 is a schematic view of a medical professional monitoring system according to the present invention and being accessed by various medical professional user sites.
Figure 2:
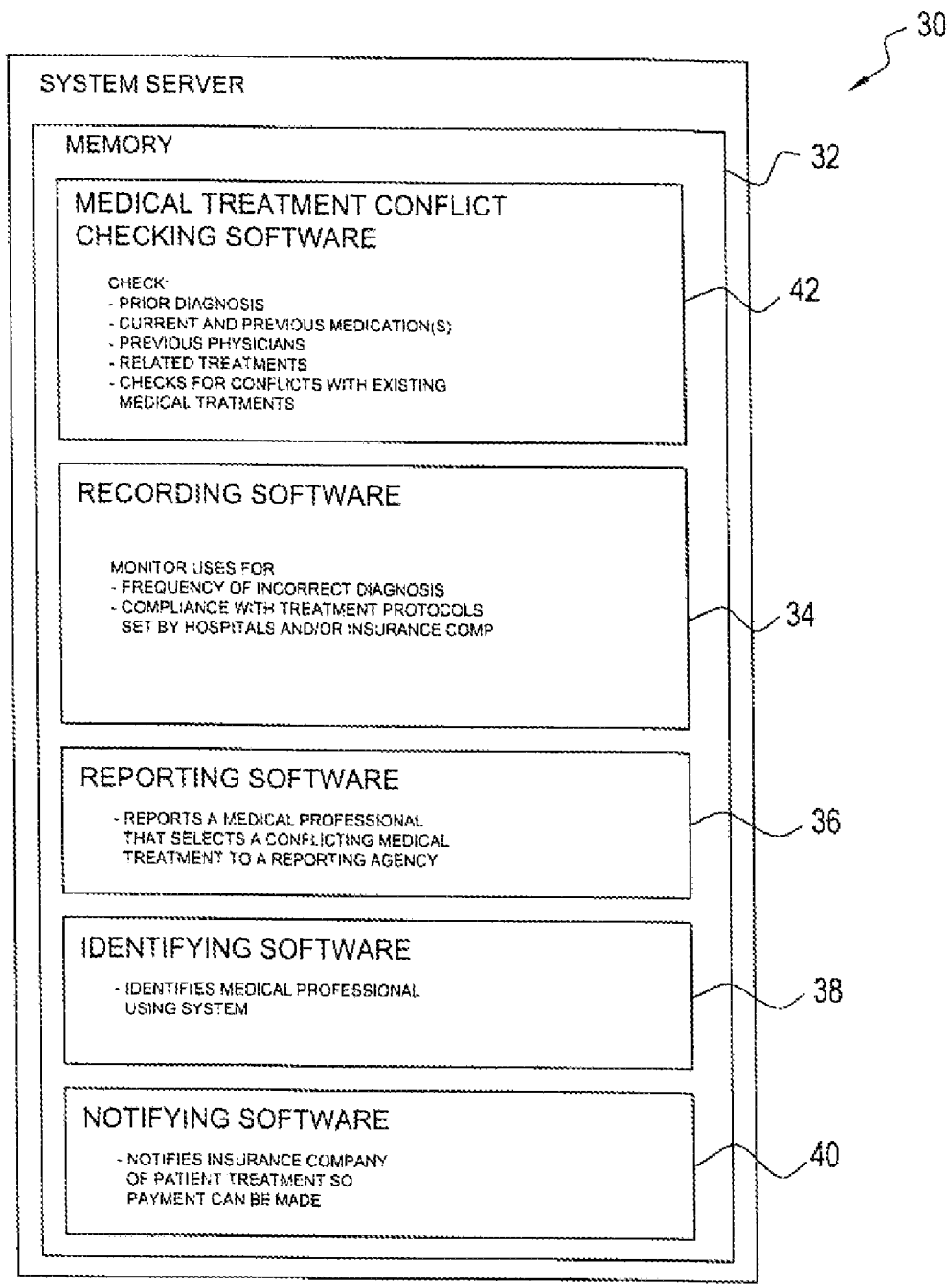
FIG. 2 is a schematic view of the server of the medical professional monitoring system illustrated in FIG. 1.
Figure 3:
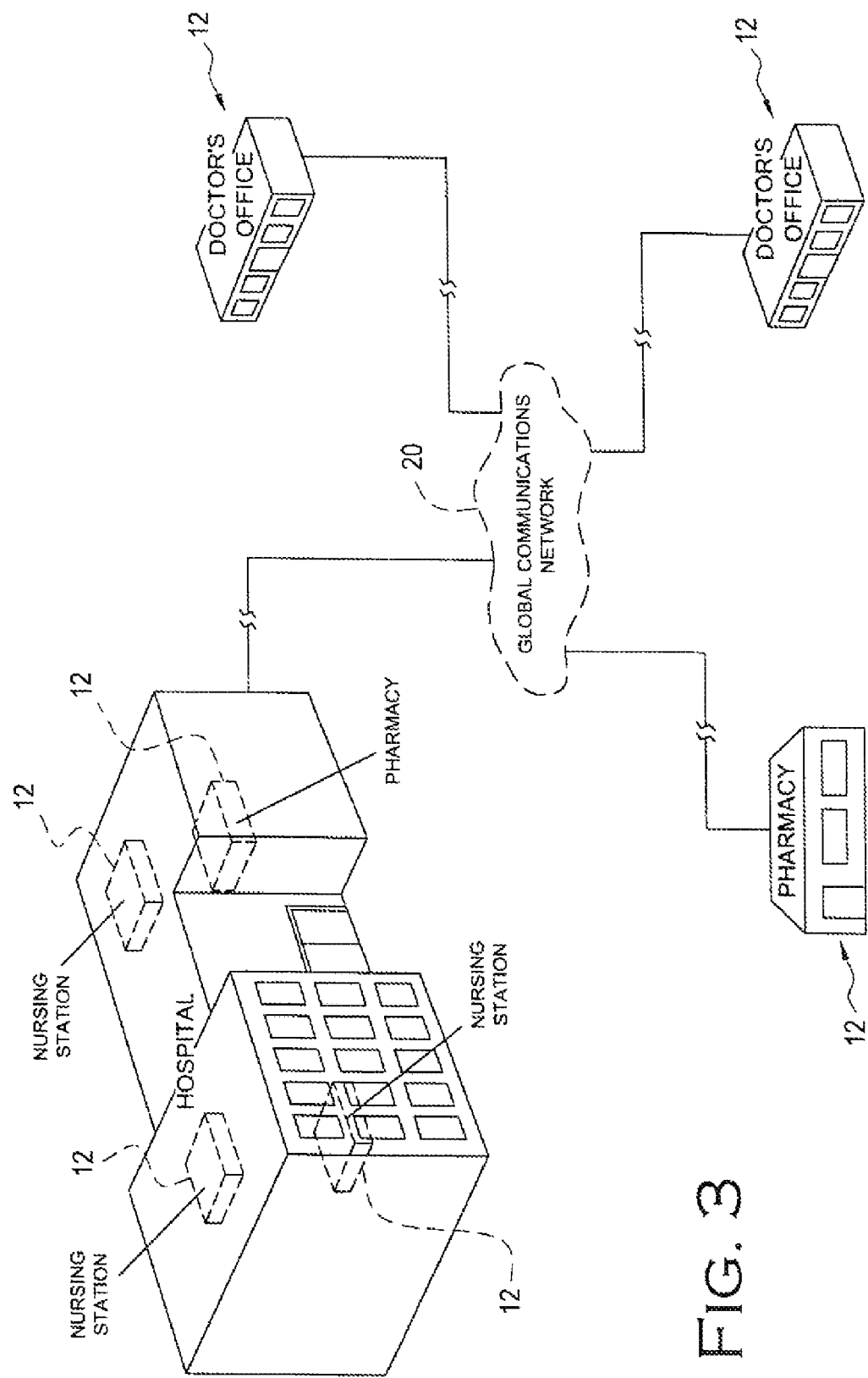
FIG. 3 is a schematic view of the medical professional monitoring system illustrated in FIG. 1 being used in a plurality of locations.
Figure 4:
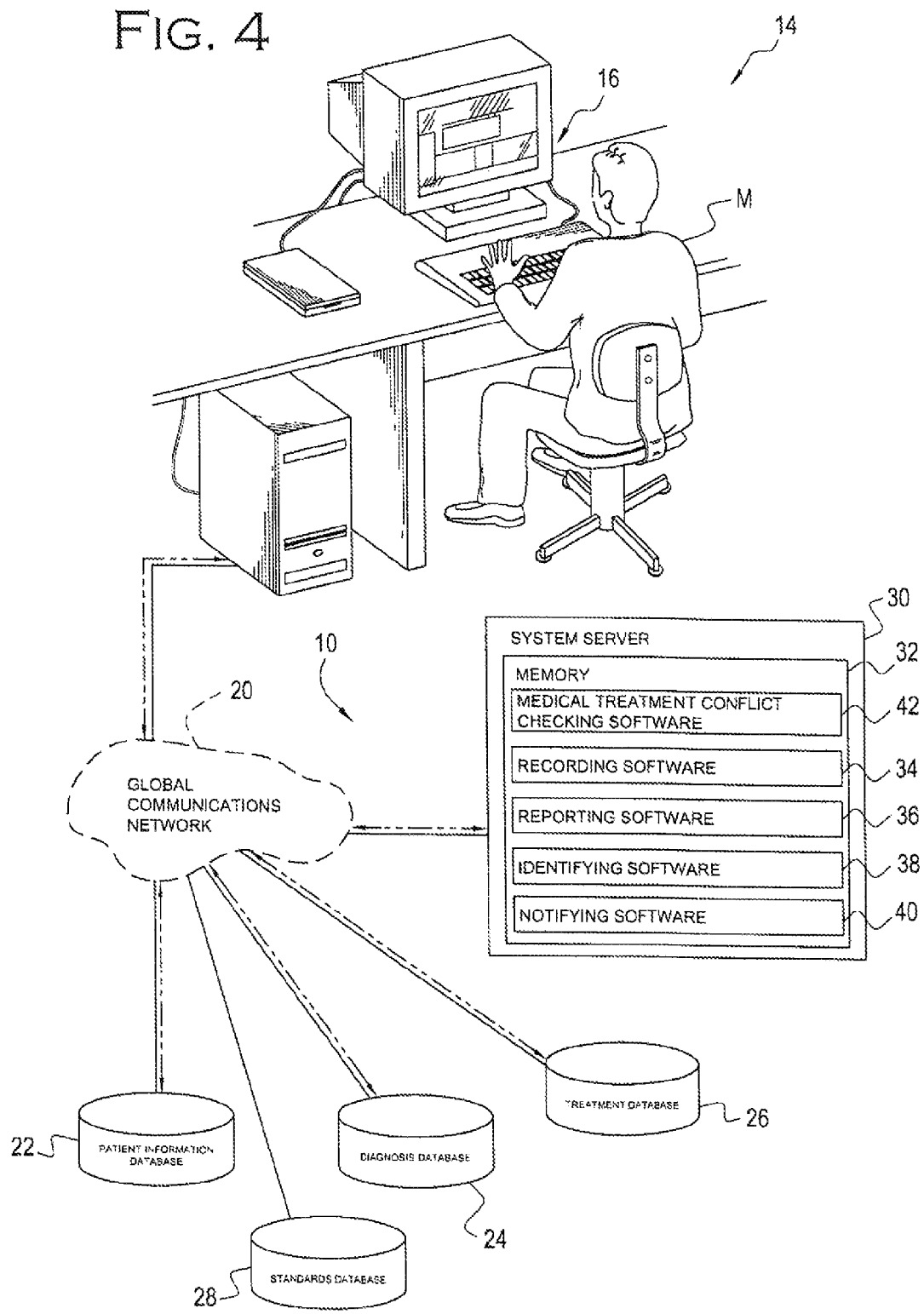
Figure 5:
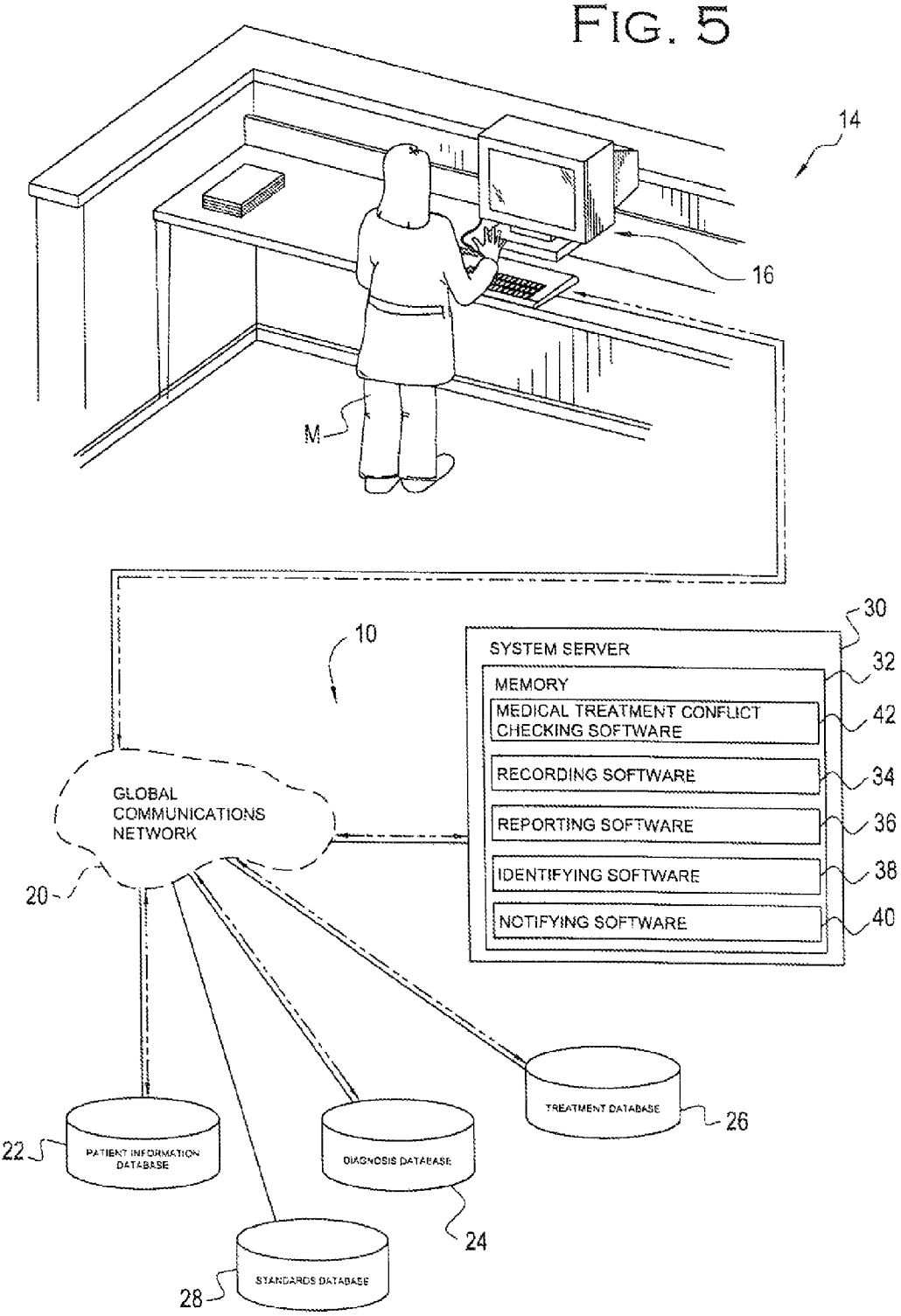

Referring initially to FIGS. 1 and 2, a medical professional monitoring system 10 according to the present invention is now described in greater detail. As illustrated in FIG. 1, the medical professional monitoring system 10 may be used in a plurality of medical professional user sites 12. Each of the medical professional user sites 12 illustratively includes a user workstation 14. Of course, each of the user workstations 14 preferably includes a user interface 16 (illustrated in FIGS. 4-6), such as a computer, for example, that is in communication with a global communications network 20, i.e., the Internet.

The user interface 16 is preferably for use by a medical professional M, and may be provided by a computer, for example. Those skilled in the art, however, will appreciate that any other type of user interface 16 may be provided to accomplish the goals of the present invention. For example, the user interface 16 may be a personal digital assistant (PDA), or any other device that may be used to communicate over a global communications network 20. Those skilled in the art will also appreciate that the user interface 16 may, for example, be provided by a scanner. This advantageously allows documents, such as patient charts, x-rays, etc. to be scanned and used in the medical professional monitoring system 10.

Some medical professionals M dictate information to be transcribed into patient charts. There currently exists voice recognition software that automatically transcribes such dictation, or that allows the medical professional to dictate information directly into a patient chart. Accordingly, the user interface 16 may be provided by a dictation-transcription device that is in communication with the global communications network 20 so that the medical professional M may dictate patient information, for example, to be used in the medical professional monitoring system 10.

The medical professional monitoring system 10 illustratively comprises a patient information database 22 in communication with the global communications network 20. The patient information database 22 preferably includes patient information for a plurality of patients. After a patient's information is entered into the patient information database 22, the patient may be defined as a registered patient. Of course, the patient information stored in the patient information database 22 is kept strictly confidential, and access to patient information is heavily monitored to ensure patient privacy.

The patient information database 22 is accessible by medical professionals M. Further, the patient information database 22 may include such information as past patient medical history, patient address, prescriptions history, or any other type of patient information that may be necessary for a medical professional M to make an assessment of the patient, as understood by those skilled in the art.

The medical professional monitoring system 10 also illustratively includes a diagnosis database 24 in communication with the global communications network 20. The diagnosis database 24 is accessible by medical professionals M, and may include medical diagnosis information. More specifically, medical professionals M may access the diagnosis database 24 to select one of a plurality of diagnoses based upon patient information in the patient information database 22, and further based upon analysis of the patient as presented to them.

The medical professional monitoring system 10 may advantageously be an interactive system. In other words, the monitoring system 10 may analyze information in the patient information database 22, and compare that information with information in the diagnosis database 24 to suggest one of a plurality of diagnoses. Upon reviewing the suggested diagnosis, the medical professional M may chose to accept, reject, or amend the suggested diagnosis. Of course, a medical professional M will be free to diagnose a patient with a particular diagnosis regardless of whether that diagnosis is presented to the medical professional.

Accordingly, if the patient's current medical condition as presented to the medical professional M is not updated in the patient information database 22, the medical professional may still be able to access and utilize the diagnosis information in the diagnosis database 24.

The medical professional monitoring system 10 further illustratively includes a medical treatment database 26 in communication with the global communications network 20 and accessible by medical professionals M. The medical treatment database 26 preferably includes medical treatment information that may be used by the medical professional M to select a medical treatment based on the diagnosis information retrieved from the diagnosis database 24.

Again, since the medical professional monitoring system 10 is an interactive system, the information in the patient information database 22 and the diagnosis database 24 are analyzed so that the system presents a proposed medical treatment to the medical professional M selected from the medical treatment database 26. Of course, those skilled in the art will appreciate that the medical professionals M are not limited to the medical treatments listed in the medical treatment database 26, but rather may also select medical treatments that are not listed in the medical treatment database. This advantageously allows the medical professional M a great deal of latitude to experiment with alternative medical treatments, if desired, thereby generally advancing the practice of medicine.

Some of the information in the medical treatment database 26 may be related to medications. The medication information may include proper dosing, conflict warnings and a medication conflict check to analyze medications currently being used by the patient (which should be listed in the patient information database 22) for treatment conflicts. The medication information may also include insurance coverage, affordability, other alternative medications, i.e., generic medications, and availability.

Further, various medications may be presented to the medical professional M in a predetermined order such that the most commonly prescribed medication is presented to the medical professional first. Problem medications may be flagged so that such a problem is made aware to the medical professional M before prescribing the medication.

Other medical information that may be included in the medical treatment database 26 may be directed to medical tests. More particularly, the information may include various rules that typically govern the requirements necessary before a medical test is ordered. Test options may be presented to the medical professional M, with the most common tests used for a particular diagnosis being presented to the medical professional first. The presentation of the medical tests to the medical professional M may be sorted depending upon the diagnosis, the current medications being used by the patient, contraindications, i.e., medical tests that may conflict with the patient's condition, insurance coverage, and other pertinent information, as understood by those skilled in the art.

Additional medical information that may be included in the medical treatment database 26 may be directed to medical procedures. More specifically, the information may include various rules that typically govern the requirements necessary before a medical procedure is ordered by a medical professional M. These procedures may be presented to the medical professional M for review in a particular order. This order may be dependent upon the diagnosis, other available forms of therapy, contraindications, and available insurance coverage.

The medical treatment database 26 may also include information directed to medical recommendations. More specifically, the information may include various rules that typically govern the requirements necessary before a medical professional M makes a particular medical recommendation. These recommendations may include taking no action, making a summary of previous actions for the patient, providing the patient the results of previous actions, assigning a diagnosis category to the patient, i.e., resolved, inactive, stable, etc., and communicating with other medical professionals M.

The medical professional monitoring system 10 of the present invention may advantageously coordinate work flow between various medical professionals M. More particularly, the medical professional monitoring system 10 may coordinate work flow between departments in a medical facility, i.e., between a physician and a pharmacist, or between medical professionals practicing in different areas of medicine, i.e., between a cardiologist and an anesthesiologist.

Coordination such as this advantageously enhances medical treatment by ensuring that all necessary steps are taken in the proper order when administering medical treatment. Further, this advantageously enhances medical treatment by ensuring that various steps of a proposed medical treatment are not duplicated.

The medical professional monitoring system 10 according to the present invention also illustratively includes a server 30 in communication with the global communications network 20 that is accessible by medical professionals M. Those skilled in the art will appreciate that the server 30 may either be an on-site server or an off-site server. On-site servers are advantageous from a maintenance point of view. In other words, on-site servers may advantageously be readily maintained in the office of the medical professional M. Of course, an on-site server is positioned in communication with other servers of the medical professional monitoring system 10 via the global communications network 20.

On-site servers may download updates to the medical professional monitoring system 10 from off-site servers when necessary, or any other source, as understood by those skilled in the art. More specifically, updates may be automatically sent to the on-site servers or, alternately, a medical professional M may transmit a request to an off-site server for available updates. Additional information on updating the medical professional monitoring system 10 is described in greater detail below.

The server 30 illustratively includes a memory 32 and a recording system 34 to record medical treatments selected by the medical professional M. The recording system 34 may also track the selected medical treatments for compliance with at least one predetermined standard selected from a plurality of predetermined standards.

The recording system 34 may also monitor the frequency with which a medical professional M makes an incorrect or improper diagnosis. Accordingly, a medical professional M may be rated based upon their frequency of incorrect or improper diagnoses and/or the frequency of non-compliance with the predetermined standards. Many steps are taken before it is determined that a medical professional M has made an incorrect or improper diagnosis. For example, a medical professional M may have several reasons for making a diagnosis or prescribing a particular medical treatment that may be viewed as incorrect or improper.

The medical professional monitoring system 10 of the present invention fully appreciates that medical professionals M advance the practice of medicine by experimenting with alternative medical treatments. The recording system 34 may illustratively be provided by recording software, but those skilled in the art will appreciate that any other type of system capable of recording, tracking, and/or monitoring medical treatments selected by the medical professionals M may also be suitable.

The medical professional monitoring system 10 also illustratively comprises a standards database 28 in communication with the global communications network 20. The standards database 28 preferably includes a plurality of predetermined standards. The predetermined standards are preferably medical standards, such as hospital standards, insurance standards, medical treatment standards, i.e., practice guidelines, pharmaceutical standards, medical office standards, emergency response standards, or any other type of medical standard, as understood by those skilled in the art. Those skilled in the art will also appreciate that insurance standards may be provided by insurance guidelines, such as medical necessity guidelines, coding guidelines, and approval guidelines.

The standards database 28 is preferably updatable so that new standards may be added to the standards database, and so that the new standards are recognized by the medical professional monitoring system 10. For example, hospitals may update certain standards, such as medical procedures, protocols, and acceptable medications, based on new medical research or findings. Accordingly, it is advantageous to update the standards database 28 based upon that information. Further, and also for example, as new medications become available, it may be desirable to update pharmaceutical standards in the standards database 28.

The medical professional monitoring system 10 may further include a reporting system 36. The reporting system 36 may be carried by the memory 32 of the system server 30, and may identify medical professionals M that select a medical treatment that is not compliant with at least one of the predetermined standards in the standards database 28.

The reporting system 36 may advantageously request additional information directed to a medical professional's M reason for selecting a medical treatment that is not in compliance with at least one of the plurality of predetermined standards in the standards database 28. Of course, it is not necessarily improper for a medical professional M to select a medical treatment that is not in compliance with at least one of the predetermined standards in the standards database 28. Experimentation with alternative medical treatments advantageously advances the practice of medicine.

Therefore, the medical professional monitoring system 10 of the present invention allows a medical professional M to override a proposed medical diagnosis and medical treatment. Further, after the medical professional M has selected or made a medical diagnosis for a patient's particular condition, the diagnosis and medical treatment may be cross referenced against both the information in the patient information database 22 and the standards database 28 to determined if the proposed medical procedure is a procedure that is covered by the patient's insurance, for example.

More specifically, the medical professional monitoring system 10 of the present invention advantageously includes an automated audit process. For example, and insurance company may audit a medical chart to make sure that various tests and procedures ordered by the medical professional M meet certain criteria. Of course, those skilled in the art will appreciate that this auditing process is carried out with full disclosure of the information in the medical chart. The criteria that are referenced during the auditing process may be located in the standards database 28, for example. Similarly, tests and procedures ordered by the medical professional M may also be audited for compliance with other standards set forth in the standards database 28.

Accordingly, and with reference to the auditing capabilities provided to insurance companies, the medical professional M is able to determine whether or not a procedure or test is covered by insurance prior to performing the procedure or test. More particularly, the medical professional M may determine the amount covered according to the patient's policy and the doctor's contract (or any other contract for medical services), and what can be done about the difference between the amount charged and the amount approved for payment by the insurance carrier, i.e., contractual write off, bill the patient partially or in full, etc. For example, in some cases, an insurance company may request that a medical professional M first perform a procedure before making a determination of whether the procedure is a covered procedure. If it is determined by the insurance company that the procedure is not covered, then the medical professional M may only be able to receive payment for the procedure from the patient. In some cases, the patient may be unable to pay. The auditing capabilities of the medical professional monitoring system 10 of the present invention advantageously provides both the medical professional M and the patient with knowledge and peace of mind as to whether or not the procedure will be covered by insurance prior to carrying out the procedure.

The auditing capabilities of the medical professional monitoring system 10 of the present invention are advantageously automated. This allows for determinations as to the appropriateness of a procedure and/or test to be made in a more rapid fashion. Further, automation of the auditing process advantageously enhances the efficiency of the medical professional monitoring system 10. Accordingly, the automation of the auditing process of the medical professional monitoring system 10 advantageously allows certain procedures to be pre-approved. Of course, those skilled in the art will appreciate that if it is determined that a procedure or test is not pre-approved, the patient may still have the option to move forward with the procedure.

In some cases, the medical treatment that the medical professional M determines to be the best course of action for a patient may not be affordable to the patient, i.e., the proposed medical treatment is not covered by the patient's insurance, and the patient may not have any other way to pay for the proposed treatment. The medically professional monitoring system 10 of the present invention therefore advantageously suggests alternate medical treatments to the medical professional M. Further, the medical professional monitoring system 10 also advantageously allows the patient to make a determination as to whether or not to proceed with the medical treatment.

Accordingly, the reporting system 36 may advantageously determine if a deviation in medical treatment from at least one of the predetermined standards in the standards database 28 produces a better result, i.e., an improvement in medical treatment. If, however, it is determined that the proposed medical treatment does not produces a better treatment result, and it is not in compliance with at least one of the standards in the standards database, then the medical professional M that is prescribing the particular medical treatment may be identified by the reporting system 36. After such a medical professional M is identified by the reporting system 36, the medical professional may be reported to a reporting agency. In some cases, the reporting system 36 may monitor the outcome of a prescribed medical treatment, and may make a report based on the outcome. To monitor the outcome of a prescribed medical treatment, it may be necessary for a medical professional M, or other user of the system 36 to input the outcome of the treatment.

The reporting agency is preferably provided by a quality assurance department that may be found in a medical facility. Those skilled in the art, however, will also appreciate that the reporting agency may, for example, be a hospital administrator, a medical professional review board, or any other type of reporting agency that monitors the fitness of a medical professional M. The reporting system 36 may illustratively be provided by reporting software, but those skilled in the art will appreciate that any other type of system capable of reporting information regarding a medical professional M to a reporting agency may also be suitable.

A processor (not shown) may be used to process information on the server 30 of the medical professional monitoring system 10. Accordingly, the processor may process information on the patient information database 22, the diagnosis database 24, the treatment database 26 and the standards database 28 so that a medical professional M may properly use the medical professional monitoring system 10 to provide enhanced medical care.

Use of the medical professional monitoring system 10 may begin when a medical professional M accesses and updates the patient information database 22 with patient information. This can be patient information that the medical professional M obtains from the patient, or patient information that the medical professional observes. The patient information may be gathered using a question and answer format. In other words, the medical professional monitoring system 10 may present a series of questions to the medical professional M, the answers to which are used to update patient information in the patient information database 22.

Thereafter, the medical professional M may either select a medical diagnosis from the diagnosis database 24, or a processor located on the system server 30 may be used to process patient information and provide the medical professional with a diagnosis. After the medical professional M has made a determination as to a diagnosis of a patient's condition, the medical professional may engage in any number of medical treatments, such as prescribing medications, performing additional medical tests, performing medical procedures, or simply making medical recommendations. After the medical professional M has administered the medical treatment, i.e., prescribed medication, performed a procedure, made a medical recommendation, etc., the new information may be inputted into the patient information database 22 so that the patient information in the patient information database remains up to date.

All of the databases of the medical professional monitoring system 10, i.e., the patient information database 22, the diagnosis database 24, the treatment database 26 and the standards database 28, may all include a question and answer format. More particularly, a medical professional M that is using the system 10 may be presented with a question from any one of the databases in order to provide additional information that may be necessary, or to further process the patient for receipt of suitable medical care. Further, a processor located on the server 30 may automatically generate a question to be presented to the medical professional M when providing medical treatment to thereby advantageously enhance medical treatment.

After the medical professional M has made a determination as to a desired question to ask of the patient regarding the patient's medical condition, the medical professional may receive an answer from the patient that is expected and that may already exist in the database in an answer format. After the answer is properly determine the system 10 may determine if additional information is necessary, and if so, may prompt the medical professional to ask additional questions. This may advantageously assist the medical professional in narrowing a possible medical diagnosis which may be selected from the diagnosis database 24, or selecting a medical treatment, such as prescribing medications, performing additional medical tests, performing medical procedures, or simply making medical recommendations, which may be selected from the medical treatment database 26, for example. The medical professional M may thereafter update the patient information database 22 with information directed to the prescribed medical treatment.

Throughout the procedure of using the medical professional monitoring system 10 of the present invention, all of the above referenced steps are preferably validated. For example, the patient information that is inputted into the patient information database 22 may be validated as being accurate. Also for example, the diagnosis selected by the medical professional M, as well as the selected medical treatment may be validated by comparison with the predetermined standards in the standards database 26. If, during this validation process, additional information is necessary to assist in the diagnosis or treatment of the patient, the system 10 presents questions directed to obtaining the additional information to the medical professional M. The medical professional M may thereafter determine whether or not it is necessary to ask the patient those questions. In other words, the medical professional M advantageously maintains control of medical treatment. As described above, these standards, or guidelines, may, for example, include individual standards, practice standards, facility standards, and standards set by an insurance company.

The selected medical treatments may be tracked for quality assurance purposes, and errors made by a medical professional M may be reported. These errors may be reported even if the medical professional monitoring system 10 corrects the errors pursuant to information provided to the medical professional by the medical professional monitoring system. The medical treatments and procedures selected by the medical professional M may then be transmitted to an insurance company, for example, for immediate payment. Those skilled in the art will appreciate that this information does not necessarily have to be transmitted to an insurance company for payment, but rather may be transmitted to any party responsible for payment of the medical treatment and/or procedures.

The medical professional monitoring system 10 may also include a medical professional identification system 38. The medical professional identification system 38 may be carried by the memory 32 of the system server 30. More specifically, the medical professional identification system 38 preferably identifies the medical professional M that has accessed at least one of the patient information database 22, the diagnosis database 24, the treatment database 26, and the standards database 28.

The medical professional identification system 38 may illustratively be provided by identifying software, but those skilled in the art will appreciate that any other type of system capable of identifying the medical professionals M may also be suitable. The identification software may prompt a user for a user ID and a password to authenticate and identify each medical professional M accessing one of the patient information database 22, diagnosis database 24, treatment database 26, or standards database 28. This advantageously enhances security of the medical professional monitoring system 10.

The medical professional monitoring system 10 may also include a notification system 40 in communication with the global communications network 20. More specifically, the notification system 40 may be carried by the memory 32 of the systems server 30. The notification system 40 preferably notifies an insurance company of patient treatment. Accordingly, the time that it normally takes for an insurance company to transmit payment for medical treatment to the medical professional M may advantageously be decreased.

The notification system 40 may also advantageously reduce administrative costs of insurance carriers. More particularly, the notification system 40 preferably validates information as it is being transmitted to the insurance carrier. This advantageously greatly reduces administrative costs associated with validation of medical treatments or procedures when received by the insurance carrier. The notification system 40 may be provided by notifying software, or any other type of system that provides a rapid notification of medical treatment to the insurance company as understood by those skilled in the art.

The medical professional monitoring system 10 may also illustratively include a medical treatment conflict check system 42 in communication with the global communications network 20. The medical treatment conflict check system 42 may be carried by the memory 32 of the systems server 30.

The medical treatment conflict check system 42 may check a medical treatment selected by a medical professional M for any conflicts with a patient's existing medical treatments. More specifically, the medical treatment conflict check system 42 preferably checks prior diagnoses, current and previous medications, previous physicians, and related treatments. For example, the medical treatment conflict check system 42 may compare a medication prescribed by the medical professional M with patient information in the patient information database 22 to determined whether or not the patient is allergic to the medication.

The medical treatment conflict check system 42 may also identify other errors that may be caused by a lack of action on the part of the medical professional M. For example, the medical treatment conflict check system 42 may detect an incomplete medical history, an incomplete physical examination, a missed diagnosis, other needed medications that were not prescribed, other necessary medical tests that were not ordered, other needed medical procedures that were not recommended or performed by the medical professional M, and instructions that were not provided to the patient. Those skilled in the art will appreciate that other types of medical conflicts may also be checked by the medical treatment conflict check system 42.

The medical treatment conflict check system 42 may be provided by medical treatment conflict checking software, or any other type of system capable of checking for medical conflicts between existing medical treatments and new medical treatments as understood by those skilled in the art.

As discussed above, the patient information database 22, the diagnosis database 24, the medical treatment database 26, and the standards database 28 may all be updatable. Accordingly, the medical professional monitoring system 10 advantageously includes up to date information so that a medical professional M may make an appropriate diagnosis of the patient condition, and prescribe the most up to date medical treatment available.

Referring now additionally to FIGS. 3-6, several uses of the medical professional monitoring system 10 at several different medical professional user sites 12 are now described in greater detail. For example, the medical professional monitoring system 10 may be used in a physician's office (FIG. 4), in a laboratory (FIG. 5), or a pharmacy (FIG. 6), for example.

The medical professionals M may be physicians, physicians assistants, nurses, pharmacists, dieticians, laboratory technicians, emergency responders, or any other type of medical professional as understood by those skilled in the art. Further, the medical professional monitoring system 10 may, for example, be used by an emergency responder in the field.

Accordingly, the medical professional monitoring system 10 allows for communication between many medical professional user sites 12 as well as between many medical professionals M. The medical professional monitoring system 10 advantageously enhances communications between medical professionals M.

For example, a pharmacist may be instantly notified when a physician changes a patient's prescription. In some cases, a pharmacy may automatically send a patient medications. The enhanced communication between medical professionals M provided by the medical professional monitoring system 10 advantageously prevents this type of redundancy and/or waste. A pharmacy, for example, may also be enabled with the ability to check whether the medical professional M. still desires a patient to receive the medication, or if it has been cancelled or changed before dispensing.

The medical professional monitoring system 10 may, for example, also advantageously provide a physician access to several different medications available to be prescribed for a certain condition. Accordingly, the physician may be able to prescribe a generic medication, which, in turn, may save money for patients.

The medical professional monitoring system 10 may, for example, further advantageously prevent insurance fraud. For example, the enhanced communication provided by the medical professional monitoring system 10 between medical professionals M prevents non-medical professionals from accessing certain databases and making changes, e.g., calling a fraudulent prescription into a pharmacy.

The medical professional monitoring system 10 of the present invention also advantageously includes searching and indexing capabilities. For example, the searching and indexing capabilities advantageously allows a medical professional M using the medical professional monitoring system 10 to search patient information on the patient information database 22. Those skilled in the art will appreciate that the searching and indexing capability of the medical professional monitoring system 10 is secured. Accordingly, medical professionals M may advantageously access information on the system 10 in a manner that allows for the security of patient information, for example, to be maintained.

More specifically, the indexing and searching capabilities of the medical professional monitoring system 10 may operate similar to a search engine. In other words the indexing and searching capabilities allow a user of the medical professional monitoring system 10 to search for information directed to a particular patient stored on other databases, even if the databases are not a part of the medical professional monitoring system. For example, the searching and indexing capabilities of the medical professional monitoring system 10 advantageously allows a medical professional M using the medical professional monitoring system to search for patient information that may be stored on a computer system of another medical professional, even if the other medical professional is not a user of the medical professional monitoring system. Those skilled in the art will appreciate that the indexing capabilities of the medical professional monitoring system 10 allows for patient information to be located regardless of the location of the information, i.e., the information does not necessarily need to be stored at a medical facility.

Of course, privacy of patient information will always be maintained. Therefore, patient information will not be obtainable unless the patient has waived the right to privacy of the information. Further, those skilled in the art will appreciate that appropriate consent will be required before such patient information can be provided.

A medical professional M using the medical professional monitoring system 10 of the present invention in a pharmacy may advantageously search the patient information database 22 to check if a prescription is valid. Upon determining that the prescription is valid, the medical professional M may validate the prescription. This advantageously reduces fraud that may occur in the medical field, e.g., fraudulent prescriptions.

Figure 7:
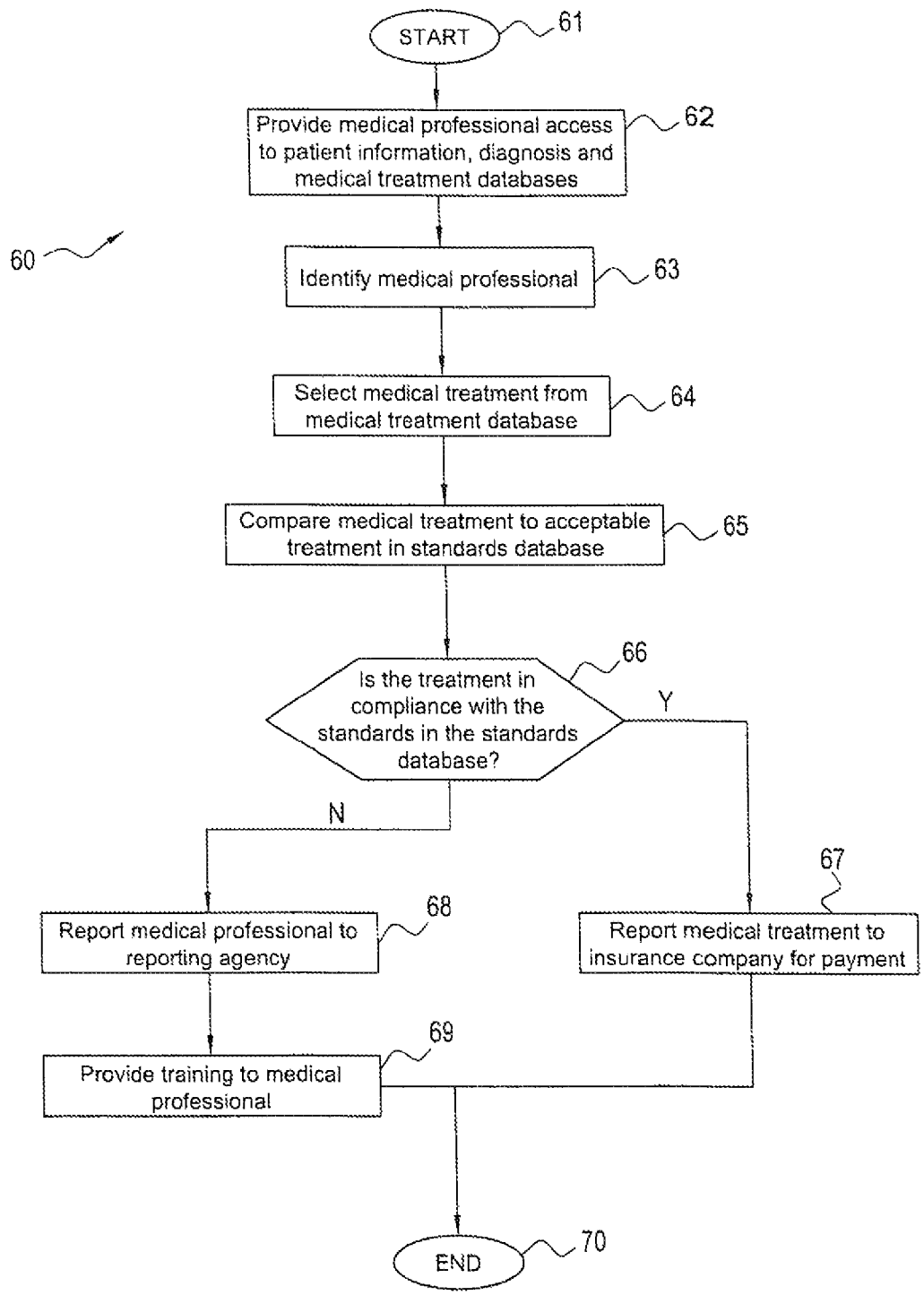
FIG. 7 is a flow chart illustrating a method for monitoring a medical professional according to the present invention.

Referring now additionally to the flow chart 60 of FIG. 7, a method of monitoring a medical professional M is now described. From the start (Block 61), a medical professional M is provided access to the patient information database 22, the diagnosis database 24, and the medical treatment database 26 at Block 62. At Block 63, the medical professional M is identified. A medical treatment is selected from the medical treatment database 26 at Block 64.

At Block 65, the medical treatment is compared to acceptable medical treatments in the standards database 28. At Block 66 it is determined whether the selected medical treatment is in compliance with the standards in the standards database 28. If it is determined at Block 66 that the selected medical treatment is in compliance with the standards in the standards database 28, then the medical treatment is reported to an insurance company for payment at Block 67. of course, those skilled in the art will appreciate that payment for medical services through an insurance company generally must be in compliance with rules and standards set forth by the insurance company. Thereafter, the method is ended at Block 70.

If, however, it is determined at Block 66 that the selected medical treatment is not in compliance with the standards in the standards database 28, then the medical professional M is reported to a reporting agency at Block 68, and training is provided to the medical professional at Block 69. Thereafter, the method is ended at Block 70.

Figure 8:
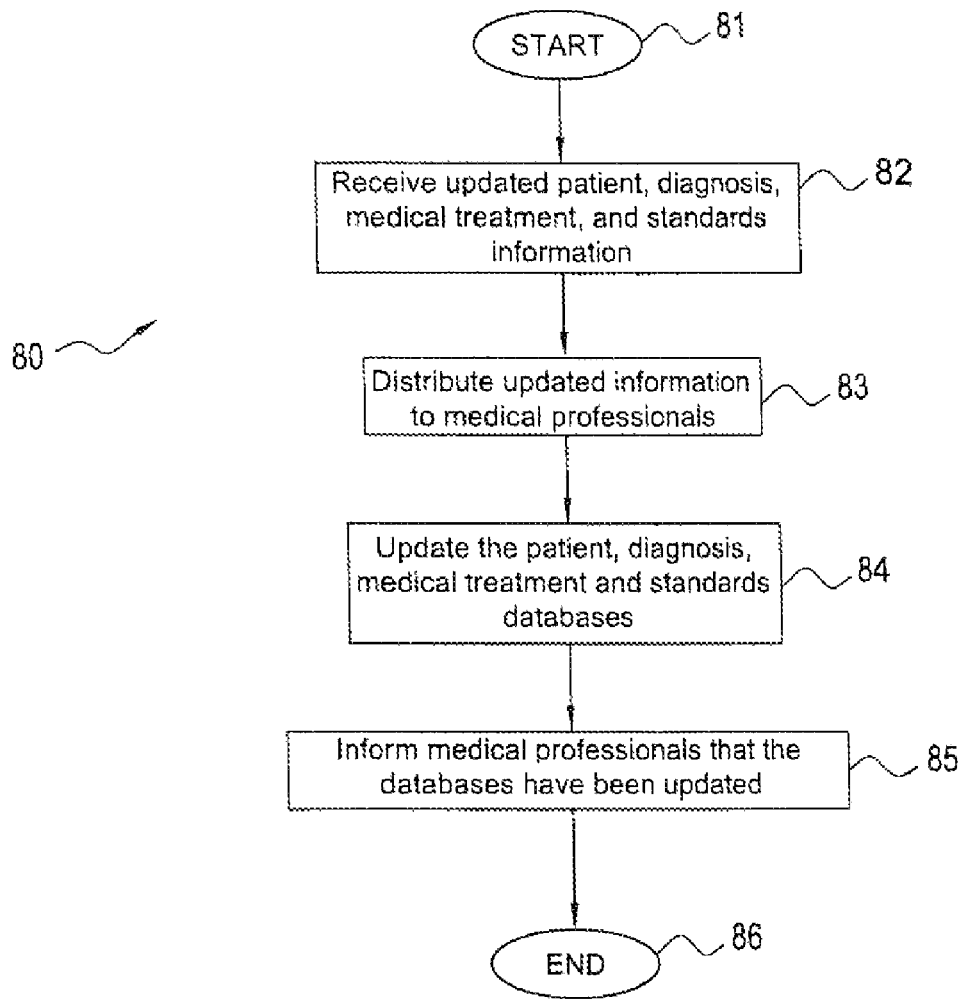
FIG. 8 is a flow chart illustrating a method for updating databases of the medical professional monitoring system according to the present invention.

Referring now additionally to the flow chart 80 of FIG. 8, a method for updating databases is now described in greater detail. From the start (Block 81), updated patient information, diagnosis information, medical treatment information, and standards information is received at Block 82. This information may be provided, for example, by consultants, committees, peer reviewers, insurance carriers, or any other agency or group related to the medical field and that may have valuable input as to proposed diagnosis, treatment, and standards information, as understood by those skilled in the art. Further, patients may provide medical professionals M with updated patient information so that the patient information database 22 may be updated.

At Block 83, the updated information is distributed to the medical professionals M. At Block 84, the patient information database 22, the diagnosis database 24, the medical treatment database 26, and the standards database 28, are updated with the new information. It is preferable that a medical professional M performs the update of the medical professional monitoring system 10, but those skilled in the art will appreciate that anyone familiar with the system, such as a system technician, for example, may also update the databases of the system. Medical professionals M are informed that the databases have been updated at Block 85. Thereafter, the method is ended at Block 86.

Figure 9:
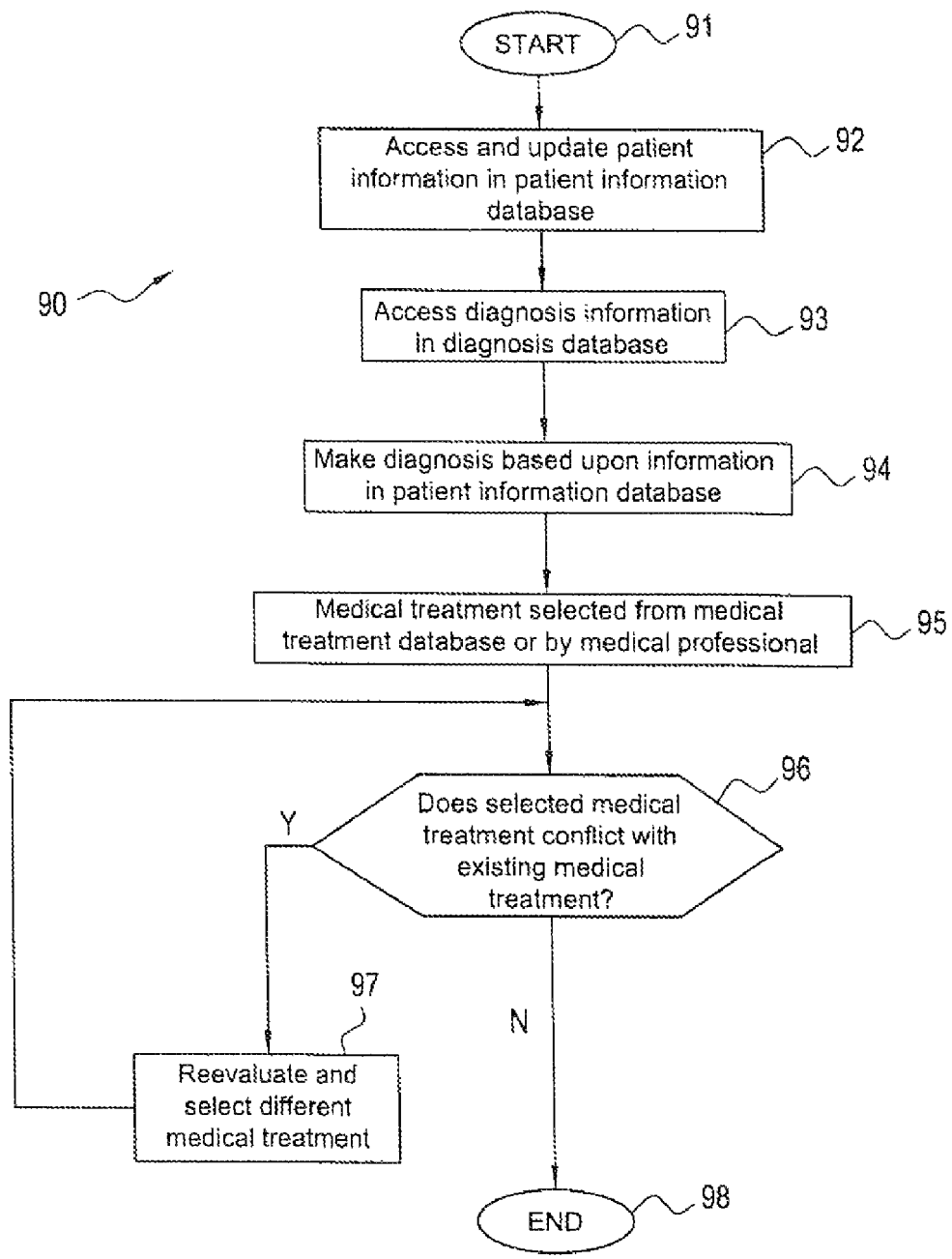
FIG. 9 is a flow chart illustrating a method for selecting a medical treatment according to the present invention.

Referring now additionally to the flow chart 90 of FIG. 9, a method for selecting a medical treatment is now described in greater detail. From the start (Block 91), patient information in the patient information database 22 is accessed and updated at Block 92. At Block 93, diagnosis information in the diagnosis database 24 is accessed. A diagnosis is made based upon information in the patient information database 22 at Block 94. At Block 95, a medical treatment is selected from the medical treatment database 26 or by a medical professional M.

At Block 96, it is determined whether the medical treatment selected from the medical treatment database 26 or by the medical professional M conflicts with a patients existing medical treatment. If it is determined at Block 96 that the selected medical treatment conflicts with a patients existing medical treatment, then the medical treatment is reevaluated at Block 97 and a different medical treatment is selected. Thereafter, it is determined whether the new medical treatment conflicts with a patient's existing medical treatment at Block 96. If a selected medical treatment does not conflict with a patient's existing medical treatment, then the method is ended at Block 98.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for assisting a medical professional with making a medical related decision related to making a diagnosis based on patient information, the method comprising:
    providing access to a plurality of databases, each of the plurality of databases containing medical related information and rules governing medical care, the plurality of databases being stored on a memory of a computer and accessible using a user interface, wherein the at least one rule provides requirements necessary for the medical professional to make the diagnosis, and wherein the diagnosis by the medical professional is not finalized until the requirements of the rules are complied with;
    searching for patient information on at least one of the plurality of databases, wherein the patient information is stored on separate database in multiple locations that provide medical services;
    providing search results from the computer of the patient information regardless of the location of the patient information so that the patient information can be used by the medical professional to make the diagnosis and applying the rules to the patient information;
    receiving the diagnosis inputted by the medical professional using the user interface;
    applying of the rules governing medical care to the patient information and to the diagnosis inputted by the medical professional;
    determining compliance or non-compliance of the diagnosis inputted by the medical professional with the rules governing medical care;
    wherein non-compliance with the requirements of the rules are included in a report with non-compliant errors presented to the medical professional using the computer prior to the diagnosis that is inputted by the medical professional is finalized so that the medical professional is prevented from making the diagnosis if the report includes an indication of non-compliance with the rules; and
    wherein compliance with the requirements of the rules governing medical care allows the diagnosis inputted by the medical professional to be finalized.

2. A method according to claim 1 further comprising auditing compliance of the patient information based on a comparison of the patient information with the at least one rule.

3. A method according to claim 2 wherein auditing compliance of the patient information is automated.

4. A method according to claim 1 wherein the plurality of databases comprise a patient information database, a diagnosis database, a medical treatment database, and a standards database.

5. A method according to claim 4 wherein the patient information is stored on the patient information database and includes at least one selected from the group comprising past medical history, past medications being taken by the patient, current medications being taken by the patient, past medical tests ordered for the patient, past and current treatment regiments for the patient and past and current diagnosis of the patient.

6. A method according to claim 1 wherein the medical related decision further comprises prescribing a medication.

7. A method according to claim 1 wherein the rules governing medical care provide requirements of the patient information that must be included in the search results prior to the medical professional prescribing a medication; and wherein the medical professional is prevented from prescribing the medication if the patient information included in the search results is not in compliance with the rules.

8. A method according to claim 1 wherein the rules governing medical care provide requirements of the patient information that must be included in the search results prior to the medical professional making a medical recommendation; and wherein the medical professional is prevented from making the medical recommendation if the patient information included in the search results is not in compliance with the rules.

9. A method for assisting a medical professional with making a medical related decision related to ordering a medical test based on patient information, the method comprising:
    providing access to a plurality of databases, each of the plurality of databases containing medical related information and rules governing medical care, the plurality of databases being stored on a memory of a computer and accessible using a user interface, wherein the at least one rule provides requirements necessary for the medical professional to order the medical test, and wherein the medical professional cannot finalize ordering the medical test until the requirements of the at least one rule are complied with;
    searching for patient information on at least one of the plurality of databases, wherein the patient information is stored on separate databases in multiple locations that provide medical services;
    receiving the order for the medical test inputted by the medical professional using the user interface;
    applying at least one of the rules to the patient information and to the medical test inputted by the medical professional;
    determining compliance or non-compliance of the medical test with the rules governing medical care;
    auditing compliance of the patient information based on a comparison of the patient information with at least one of the rules, and wherein auditing compliance of the patient information is automated;
    wherein non-compliance with the requirements of the rules are included in a report with non-compliant errors presented to the medical professional using the computer prior to the medical test being ordered so that the medical professional is prevented from ordering the medical test if the report includes an indication of non-compliance with the rules;
    wherein compliance with the requirements of the rules governing medical care allows the medical test ordered by the medical professional to be finalized; and
    wherein non-compliance of the patient information with the rules as determined when the patient information is audited are included in the report with non-compliant errors.

10. A method according to claim 9 further comprising providing search results from the computer of the patient information regardless of the location of the patient information.

11. A method according to claim 9 wherein the plurality of databases comprise a patient information database, a diagnosis database, a medical treatment database, and a standards database.

12. A method according to claim 11 wherein the patient information is stored on the patient information database and includes at least one selected from the group comprising past medical history, past medications being taken by the patient, current medications being taken by the patient, past medical tests ordered for the patient, past and current treatment regiments for the patient and past and current diagnosis of the patient.

13. A method according to claim 9 wherein the medical related decision further comprises prescribing a medication.

14. A method according to claim 9 wherein the at least one rule governs patient information necessary to be located before a medication may be prescribed.

15. A method according to claim 9 wherein the rules governing medical care provide requirements of the patient information that must be included in the search results prior to the medical professional providing a medical recommendation; and wherein the medical professional is prevented from making the medical recommendation if the patient informant included in the search results is not in compliance with the rules.

16. A system for assisting a medical professional in making a medical related decision directed to at least one of making a diagnosis, ordering a medical test, and recommending a medical procedure based on patient information, the system comprising:
   at least one user interface;
   a plurality of databases stored on a memory and each accessible using said at least one user interface, at least one of the plurality of databases containing patient information and rules governing patient information wherein the rules provide requirements necessary for the medical professional to make the medical related decision directed to at least one of making the diagnosis, ordering the medical test, and recommending the medical procedure, and wherein the medical related decision directed to at least one of making the diagnosis, ordering the medical test, and recommending the medical procedure is not finalized until the requirements of the rules are complied with; and
   an auditing system in communication with the plurality of databases;
   wherein the plurality of databases are searched for patient information that is stored on separate databases in multiple locations that provide medical service:
   wherein search results are provided of the patient information regardless of the location of the patient information so that the patient information can be used by the medical professional to make the medical related decision by applying at least one of the rules to the patient information;
   wherein at least one of the rules is applied to the patient information and to the medical related decision directed to at least one of making the diagnosis, ordering the medical test, and recommending the medical procedure, wherein the patient information is searched on at least one of the plurality of databases, wherein the patient information is stored on separate databases in multiple locations providing medical services, and wherein the auditing system audits the patient information for compliance with the rules;
   wherein compliance or non-compliance of the medical related decision with the requirements of the rules is determined and wherein an indication is provided to the medical professional of compliance or non-compliance of the patient information with the rules prior to the medical related decision being finalized;
   wherein non-compliance of the patient information with the rules results in display of a report with non-compliant errors being viewable by the medical professional so that the medical professional cannot finalize the medical related decision directed to at least one of making the diagnosis, ordering the medical test, and recommending the medical procedure and so that the medical professional is prevented from making the medical related decision if a report is provided that includes an indication of non-compliance with the rules; and
   wherein compliance of the patient information with the rules allows the medical related decision made by the medical professional to be finalized 17. A system according to claim 16 wherein the auditing system is automated to assess compliance of the patient information based on a comparison of the patient information with the at least one rule.

18. A system according to claim 16 wherein the plurality of databases comprises a patient information database, a diagnosis database, a medical treatment database, and a standards database.

19. A system according to claim 18 wherein the patient information is stored on the patient information database and includes at least one selected from the group comprising past medical history, past medications being taken by the patient, current medications being taken by the patient, past medical tests ordered for the patient, past and current treatment regiments for the patient and past and current diagnosis of the patient.

20. A system according to claim 16 wherein the medical related decision further comprises prescribing a medication.

21. A system according to claim 16 wherein the rules govern patient information necessary to be located before a medication may be prescribed.

22. A system according to claim 16 wherein the rules govern patient information necessary to be located before a medical recommendation may be provided.

23. A method for assisting a medical professional with making a medical related decision related to recommending a medical procedure, the method comprising:
   providing access to a plurality of databases, each of the plurality of databases containing medical related information and rules governing medical care, the plurality of databases being stored on a memory of a computer and accessible using a user interface, wherein the at least one rule provides requirements necessary for the medical professional to recommend the medical procedure, and wherein the medical professional cannot finalize recommending the medical procedure until the requirements of the at least one rule are complied with;
   searching for patient information on at least one of the plurality of databases, wherein the patient information is stored on separate databases in multiple locations that provide medical services;
   receiving the medical related decision related to recommending the medical procedure inputted by the medical professional using the user interface;
   applying at least one of the rules to the patient information and to the medical related decision related to recommending a medical procedure inputted by the medical professional;

determining compliance or non-compliance of the medical related decision related to recommending a medical procedure with the rules governing medical care;

auditing compliance of the patient information based on a comparison of the patient information with the at least one of the rules, wherein auditing compliance of the patient information is automated;

wherein non-compliance with the requirements of the rules are included in a report with non-compliant errors presented to the medical professional using the computer prior to the medical related decision related to recommending a medical procedure is made so that the medical professional is prevened from making the medical related decision related to recommending a medical procedure if the report includes an indication of non-compliance with the rules;

wherein compliance with the requirements of the rules allows the medical related decision related to recommending a medical procedure made by the medical professional to be finalized; and wherein non-compliance of the patient information with the rules as determined when the patient information is audited are included in the report with non-compliant errors.

24. A method according to claim 23 further comprising providing search results from the computer of the patient information regardless of the location of the patient information.

25. A method according to claim 23 wherein the plurality of databases comprise a patient information database, a diagnosis database, a medical treatment database, and a standards database.

26. A method according to claim 25 wherein the patient information is stored on the patient information database and includes at least one selected from the group comprising past medical history, past medications being taken by the patient, current medications being taken by the patient, past medical tests ordered for the patient, past and current treatment regiments for the patient and past and current diagnosis of the patient.

27. A method according to claim 23 wherein the medical related decision further comprises prescribing a medication.

28. A method according to claim 23 wherein the at least one rule governs patient information necessary to be located before a medication may be prescribed.

29. A method according to claim 23 wherein the at least one rule governs patient information necessary to be located before a medical recommendation may be provided.

* * * * *